US008208652B2

(12) United States Patent
Keady

(10) Patent No.: US 8,208,652 B2
(45) Date of Patent: Jun. 26, 2012

(54) METHOD AND DEVICE FOR ACOUSTIC SEALING

(75) Inventor: John Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 612 days.

(21) Appl. No.: 12/360,001

(22) Filed: Jan. 26, 2009

(65) Prior Publication Data
US 2009/0238374 A1 Sep. 24, 2009

Related U.S. Application Data

(60) Provisional application No. 61/023,828, filed on Jan. 25, 2008.

(51) Int. Cl.
*A61F 11/06* (2006.01)
(52) U.S. Cl. .......................... 381/72; 381/328
(58) Field of Classification Search .............. 381/69, 381/72
See application file for complete search history.

(56) References Cited

U.S. PATENT DOCUMENTS

| | | | |
|---|---|---|---|
| 2,535,258 A | 12/1950 | Bland | |
| 3,602,654 A | 8/1971 | Victoreen | |
| 4,741,344 A | 5/1988 | Danby et al. | |
| 4,834,211 A * | 5/1989 | Bibby et al. | 181/135 |
| 4,896,679 A | 1/1990 | St. Pierre | |
| 4,962,537 A | 10/1990 | Basel et al. | |
| 5,333,622 A | 8/1994 | Casali et al. | |
| 5,483,027 A | 1/1996 | Krause | |
| 6,094,494 A | 7/2000 | Haroldson | |
| 6,256,396 B1 | 7/2001 | Cushman | |
| 6,339,648 B1 | 1/2002 | McIntosh et al. | |
| 6,393,130 B1 | 5/2002 | Stonikas et al. | |
| 6,671,381 B1 | 12/2003 | Lux-Wellenhof | |
| 7,130,437 B2 | 10/2006 | Stonikas et al. | |
| 7,164,775 B2 | 1/2007 | Meyer et al. | |
| 7,227,968 B2 | 6/2007 | van Halteren et al. | |
| 7,362,875 B2 | 4/2008 | Saxton et al. | |
| 7,387,187 B2 | 6/2008 | Widmer et al. | |
| 2006/0159298 A1 | 7/2006 | von Dombrowski et al. | |
| 2007/0116319 A1 | 5/2007 | Hagberg | |
| 2008/0144871 A1 | 6/2008 | Purcell et al. | |
| 2009/0173353 A1 | 7/2009 | Purcell et al. | |
| 2009/0320858 A1 | 12/2009 | Purcell et al. | |
| 2009/0320859 A1 | 12/2009 | Purcell et al. | |

* cited by examiner

*Primary Examiner* — Kiesha Bryant
*Assistant Examiner* — Paul Patton
(74) *Attorney, Agent, or Firm* — RatnerPrestia

(57) ABSTRACT

Acoustic reflective devices are provided. An acoustic reflective device is configured to be inserted into an orifice. The device includes a stressing device that can vary a volume in response to a voltage difference across a portion of the stressing device. The stressing device is at least partially surrounded by a membrane.

10 Claims, 7 Drawing Sheets

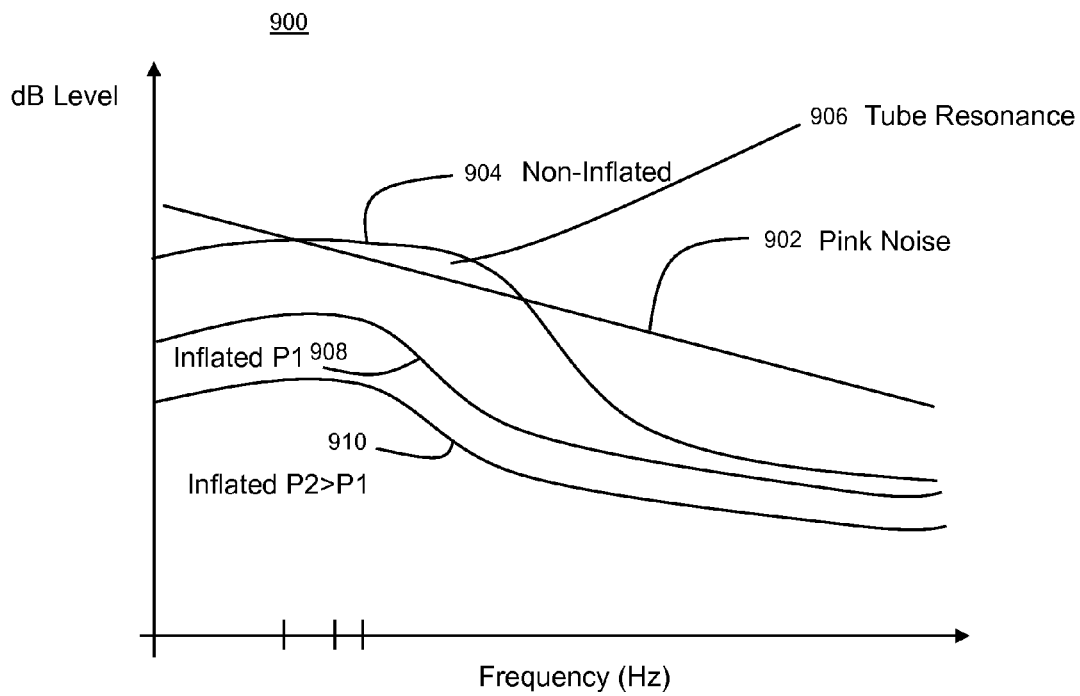
FIG. 9 semi-log plot
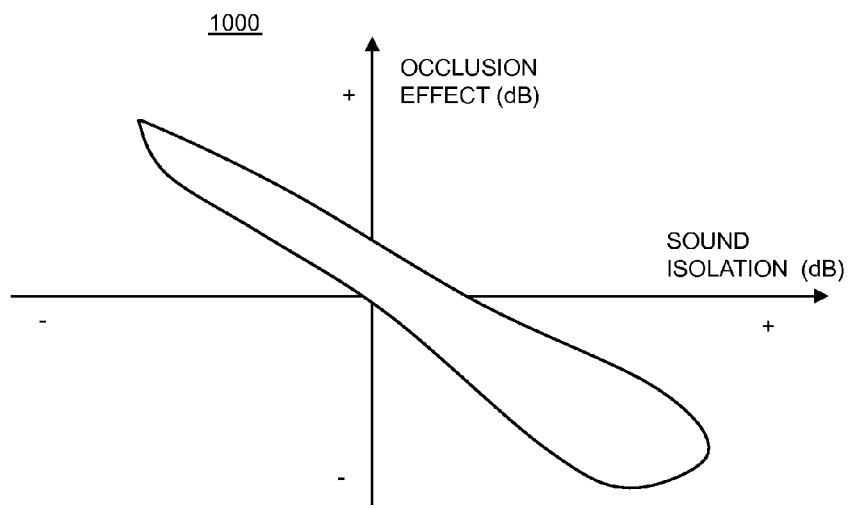
FIG. 10

METHOD AND DEVICE FOR ACOUSTIC SEALING

CROSS-REFERENCE TO RELATED APPLICATIONS

This application claims the benefit of U.S. provisional patent application No. 61/023,828 filed on 25 Jan. 2008. The disclosure of which is incorporated herein by reference in its entirety.

FIELD OF THE INVENTION

The present invention relates to devices that can be inserted into orifices and more particularly, though not exclusively, a device that can be inserted into body orifices and provides a measure of acoustic isolation.

BACKGROUND OF THE INVENTION

With the advent of an industrial society, people are exposed to noise pollution at greater and greater levels; both from background, such as street traffic, airplanes, construction sites and intentional exposure to high sound levels such as cell phones, MP3 players, and rock concerts. Studies show that ear damage, leading to permanent hearing impairment is not only increasing in the general population, but increasing at a significantly faster rate in younger populations.

The potential for hearing damage is a function of both the level and the duration of exposure to the sound stimulus. Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise.

Devices have been developed over the years to reduce sound from entering the ear canal. These devices known as earpieces, typically fit into the ear or around the ear. For example, headphones, earbuds, behind the ear earpieces, hearing aids, headsets and other devices attenuate sound from the ambient environment and direct acoustic energy to the tympanic membrane of the ear. People typically do not have knowledge of the cumulative sound levels that they receive on a daily basis. Moreover, both short term and long term noise exposure can be a health risk. Accordingly, a system that overcomes the shortcomings in the related art would be useful.

BRIEF DESCRIPTION OF THE DRAWINGS

Exemplary embodiments of the present invention will become more fully understood from the detailed description and the accompanying drawings, wherein:

FIG. 9 is a graph illustrating sound isolation as a function of inflation of an inflatable system in accordance with at least one exemplary embodiment;

FIG. 10 is a graph of sound isolation versus occlusion effect in accordance with at least one exemplary embodiment;

DETAILED DESCRIPTION OF EXEMPLARY EMBODIMENTS OF THE PRESENT INVENTION

Figure 1:
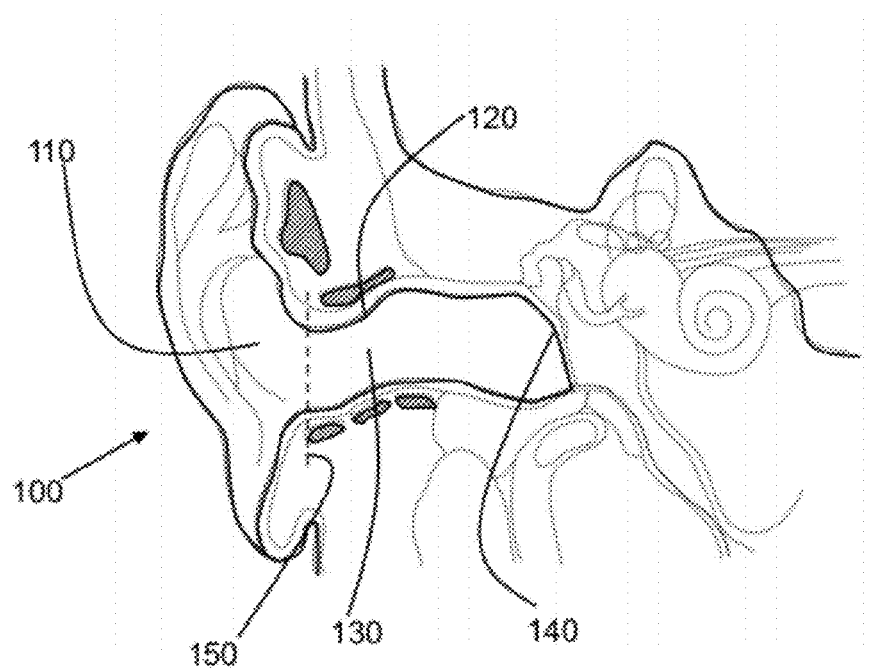
FIG. 1 illustrates general physiology of an ear.

The following description of exemplary embodiment(s) is merely illustrative in nature and is in no way intended to limit the invention, its application, or uses.

Exemplary embodiments are directed to or can be operatively used on various wired or wireless earpieces devices (e.g., earbuds, headphones, ear terminal, behind the ear devices or other acoustic devices as known by one of ordinary skill, and equivalents). For example, the earpieces can be without transducers (for a noise attenuation application) or one or more transducers (e.g. ambient sound microphone (ASM), ear canal microphone (ECM), ear canal receiver (ECR)) for monitoring/providing sound. In all of the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein.

Notice that similar reference numerals and letters refer to similar items in the following figures, and thus once an item is defined in one figure, it may not be discussed or further defined in the following figures. Processes, techniques, apparatus, and materials as known by one of ordinary skill in the relevant art may not be discussed in detail but are intended to be part of the enabling description where appropriate.

FIG. 1 illustrates general physiology of an ear. The ear comprises a pinna 100, concha 110, ear canal wall 120, and tympanic membrane 140. Pinna 100 is an external portion of the ear. Pinna 100 is a cartilaginous region of the ear that focuses acoustic information from an ambient environment to an ear canal 130. Concha 110 is also an external portion of the ear. Concha 110 is a bowl shaped region in proximity to the ear canal opening.

A dashed line 150 indicates an opening to the ear where sound enters to be received by tympanic membrane 140. The ear canal wall 120 forms an acoustic chamber known as ear canal 130. Ear canal shapes and sizes vary substantially over the human population. Ear canal 130 terminates in tympanic membrane 140. Tympanic membrane 140 is a flexible membrane in the middle ear that couples to components of the inner ear. In general, the acoustic information resident in ear canal 130 vibrates tympanic membrane 140 that is converted to a signal (corresponding to the sound) that is provided to the auditory nerve.

Figure 2:
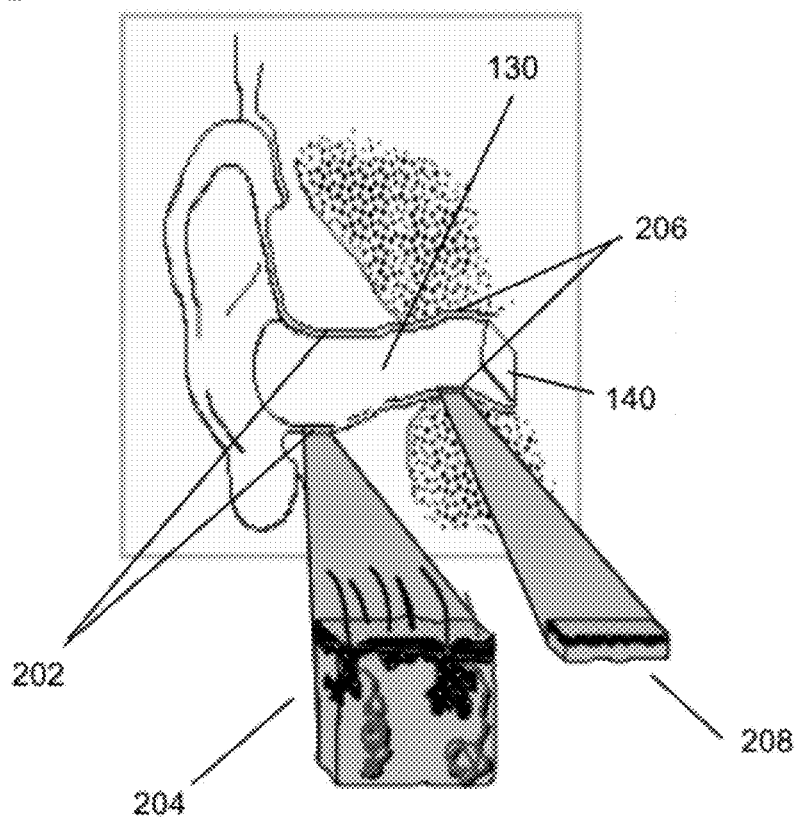
FIG. 2 illustrates a cartilaginous region and a bony region of an ear.

FIG. 2 illustrates an ear canal wall region 202 and an ear canal wall region 206 of ear canal wall 120. Ear canal wall region 206 is defined as the area where bone underlies the ear canal wall. As shown, region 206 is located in a second portion of the ear canal near the tympanic membrane 140. The skin layer of ear canal wall 120 in region 206 is sensitive to pressure. The skin layer in region 206 is approximately one tenth the thickness of the skin in ear canal wall region 202. Thus, there is not much tissue separating skin from bone. Placing an object such as an ear plug in this region can stimulate nerves due to skin being pressed against bone which can be uncomfortable and even induce significant pain. Another fact is that region 206 can radiate sound into ear canal 130 as vibrations are conducted through bone and radiated as sound into ear canal 130.

Ear canal wall region 202 is located in a first portion of ear canal 130 closest to the ear opening. Region 202 is a portion of the ear canal wall 120 that includes a layer of cartilage underlying the skin layer. Region 202 is a highly flexible region having no substantial rigid structure. A difference between regions 202 and 206 is illustrated in an exploded view of tissue 204 and tissue 208. Tissue 204 of region 202 is approximately ten times thicker than tissue 208 of region 206. The cartilage and skin of region 202 is flexible thereby making this region somewhat elastic relative to region 206. Thus, region 202 can be deformed when a force is applied to the area. In general, region 202 is much more insensitive to pressure (comfort/pain) than region 206. It should be noted that applying pressure to ear canal wall 120 such that ear canal wall 120 is deformed stretches and places the skin under tension.

Figure 3:
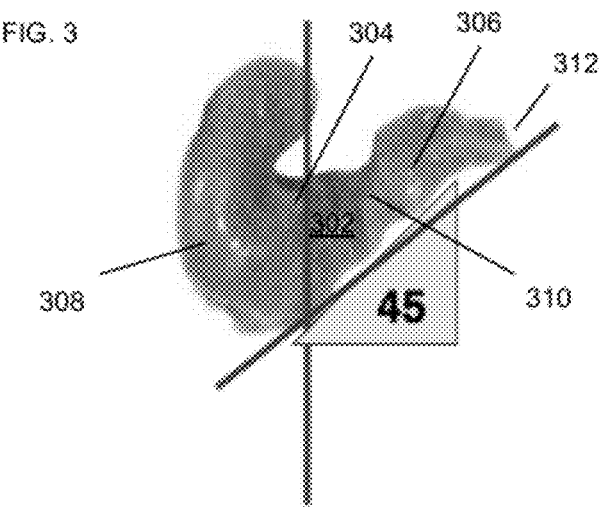
FIG. 3 is an illustration of an ear canal.

FIG. 3 is an illustration of an ear canal 302. The illustration is a mold of an ear canal 310 in an orientation looking towards the face on an individual. The mold also includes the concha bowl 308, which is a portion of the outer ear. Ear canal 302 has an upward tilt of approximately 45 degrees from the horizontal such that tympanic membrane 312 is above an ear canal opening. In general, an ear canal is not straight or regularly shaped. Ear canal 302 typically has a first bend 304 near the ear canal entrance and a second bend 306 that is proximate to tympanic membrane 312. It should be noted that the volume, shape, and length of ear canal 302 can vary substantially from person to person. Thus, there has been difficulty in providing a system that can effectively seal the ear, attenuate noise, mitigate occlusion effect, works under different environmental conditions, and fits a majority of the population. For example, hearing aid manufacturers have resorted to a full custom earpiece for individuals where a mold of the user's ear canal is made for forming a housing. The time and cost of this process is quite expensive.

Figure 4:
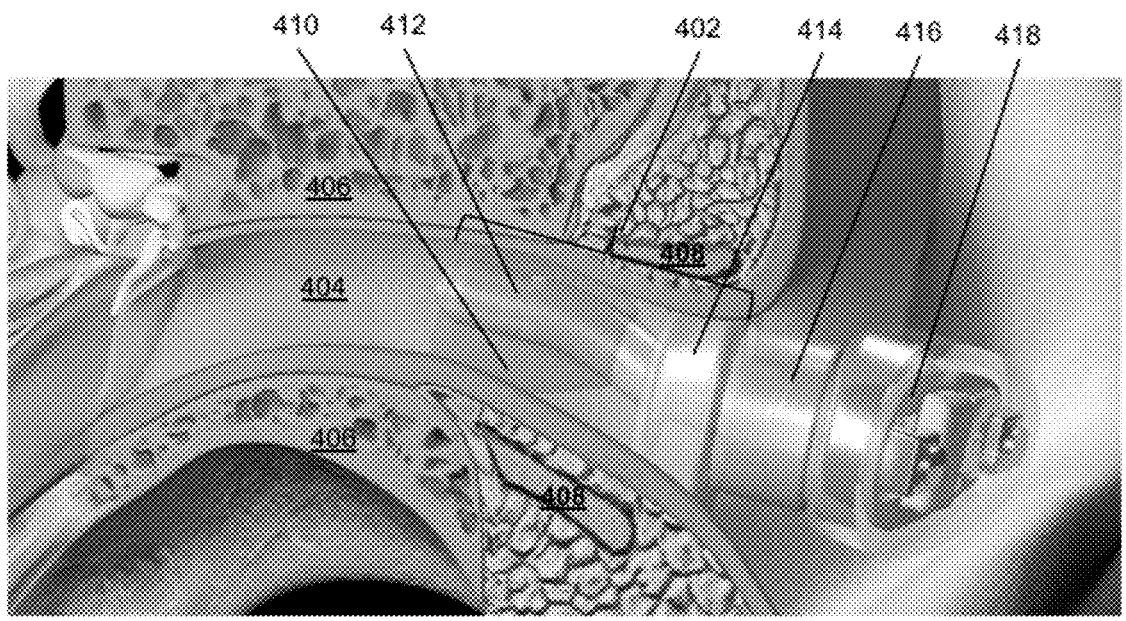
FIG. 4 is an illustration of an earpiece inserted in an ear canal in accordance with at least one exemplary embodiment.

FIG. 4 is an illustration of an earpiece inserted in an ear canal 404 in accordance with at least one exemplary embodiment. The earpiece comprises a sealing section 402 for sealing the ear, a first housing 416, and a second housing 418. Sealing section 402 creates an ear canal volume 404 that is isolated from an ambient environment. Sealing section 402 reduces sound from the ambient environment from reaching ear canal volume 404 through two paths. The first path is the opening to the ear canal, which is sealed. The second path for sound to enter ear canal volume 404 is through bone conduction. The second path can provide significant acoustic energy to ear canal volume 404 when the wearer of the earpiece speaks. How sealing section 402 reduces sound from reaching ear canal volume 404 will be discussed in greater detail hereinbelow.

Sealing section 402 comprises a first section 410 and a second section 414. Second section 414 prevents a user of the earpiece from inserting the device too deeply into the ear canal. Second section 414 is designed to be larger than a majority of ear openings but can have a region that fits and seals the ear canal opening.

First section 410 is inserted or inflated in the ear canal leaving ear canal volume 404 remaining. First section 410 contacts an ear canal wall and seals the ear canal. As shown, first section 410 can contact both a bony region 406 and a cartilaginous region 408 of the ear canal. In at least one exemplary embodiment, a surface of first section 410 in contact with the ear canal wall is under tensile stress. Furthermore, a radial force is applied to first section 410 to hold the surface against the ear canal wall. As shown, first section 410 can be formed on a stent 412 having none (e.g., earplug design) or one or more acoustic channels for providing and receiving sound.

In at least one exemplary embodiment, first housing 416 houses components of the earpiece. For example, first housing 416 (and second housing 418) can include at least one ear canal receiver and/or at least one ear canal microphone. The ear canal receiver is a speaker that is coupled to an acoustic channel of stent 412 for providing sound to ear canal volume 404. Similarly, the ear canal microphone is coupled to an acoustic channel of stent 412 for receiving sound in ear canal volume 404. Furthermore, first housing 416 can house components for increasing or decreasing a volume of first section 410. For example, the volume of first section 410 is reduced to simplify removal and or insertion of sealing section 402 from the ear canal. Conversely, first section 410 is expanded for sealing the ear canal after an insertion process.

Housing 418 includes further components of the earpiece system. An ambient sound microphone can be placed in housing 418 for receiving sound in the ambient environment. Electronic components for managing audio content, modifying audio content, power management (including a battery); a/d conversion, d/a conversion, mixing, amplification, wired/wireless communication, time, and location can be included in housing 418. In general, isolating ear canal volume 404 from the ambient environment provides an opportunity to monitor sound in the ear canal. By monitoring sound received by the user of the system, an action can be taken to mitigate potential hearing damage should sound levels in the short term or over a longer period of time pose a risk to the user. Isolation from the ambient environment from a hearing perspective can result in reduced situation awareness. For example, people listening to music with an earpiece are often not cognizant of potential dangers in the ambient environment that they would normally recognize (e.g. siren or warning). The electronic components in housing 418 can be used to identify and provide sounds of importance (e.g. siren or warning) to a user when picked up by the ambient sound microphone.

Figure 5:
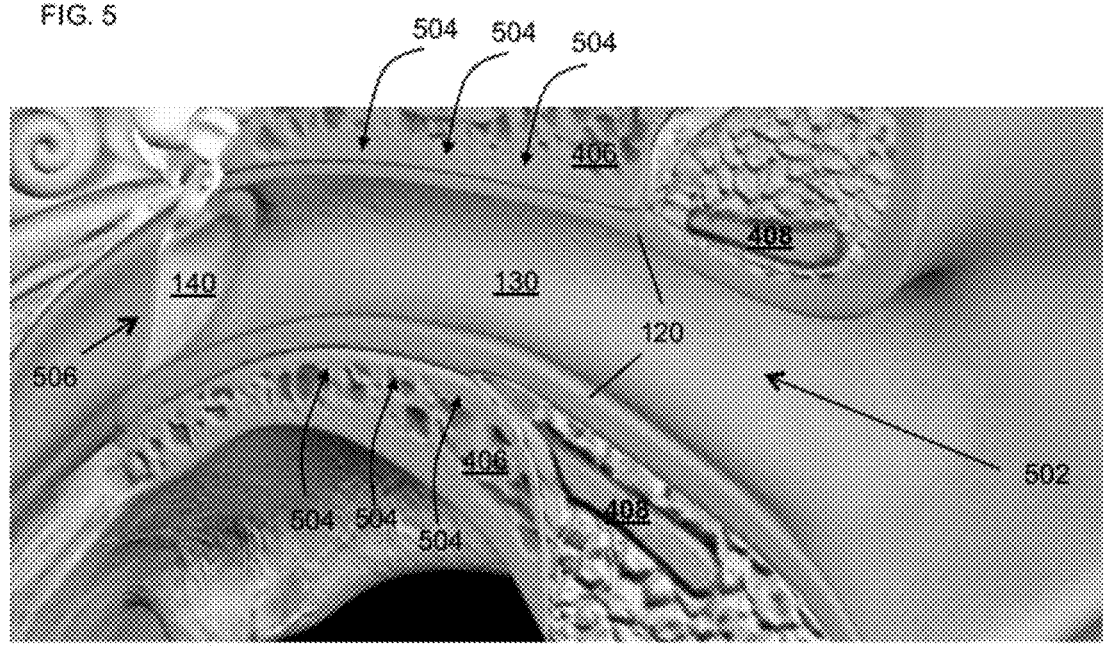
FIG. 5 is a cross sectional view of an ear canal in accordance with at least one exemplary embodiment.

FIG. 5 is a cross sectional view of an ear canal in accordance with at least one exemplary embodiment. The ear canal 130 is an acoustic channel for coupling sound to tympanic membrane 140. Sound reaches ear canal 130 through several paths. The principal path 502 for sound to enter ear canal 130 is through the ear canal opening in the outer ear.

Two other paths are illustrated that can provide sound into ear canal 130. Both paths are through the body and the path is not directly connected to the ambient environment. A path 504 provides sound through bone conduction. For example, sound generated when a person speaks vibrates bone adjacent to ear canal wall 120. The vibration corresponding to the speech is radiated through ear canal wall 120 by this secondary path and into ear canal 130. Similarly, a path 506 can provide sound to ear canal 130 from areas of the inner ear.

The sound provided through paths 504 and 506 is not significant under normal conditions where sound is coupled through the ear canal opening. Conversely, sealing the opening to ear canal 130 prevents sound from the ambient environment from entering. Under this condition the remaining portion of the ear canal is isolated from the ambient environment. The deleterious effect of sealing the ear canal manifests itself when a person speaks. Normally, speech radiates from the mouth and into a person's ears. Many of the high frequency components that we utter are generated by the complex interactions as the sound leaves our mouth. These high frequency components are missing when the speech is radiated through the body (e.g. bone conduction) and into ear canal 130. The sound is further modified due to resonance in the sealed ear canal volume, which amplifies (typically <500 Hz) or attenuates frequencies. The net result is that sound such as our voice is unfamiliar and can be disconcerting to some people and abnormally high (larger amplitude). The sound of bone-conducted speech into the ear canal is often described as lower in frequency, boomy, and muffled. Other sounds which we normally do not hear such as chewing or teeth grinding can become much more prominent when the ear is sealed. The phenomenon of resonance boosting a low frequency signal in a sealed ear canal is known as the occlusion effect. The frequency at which the signal level is increased varies as a function of the shape, volume, and other physical attributes of the ear canal.

Figure 6:
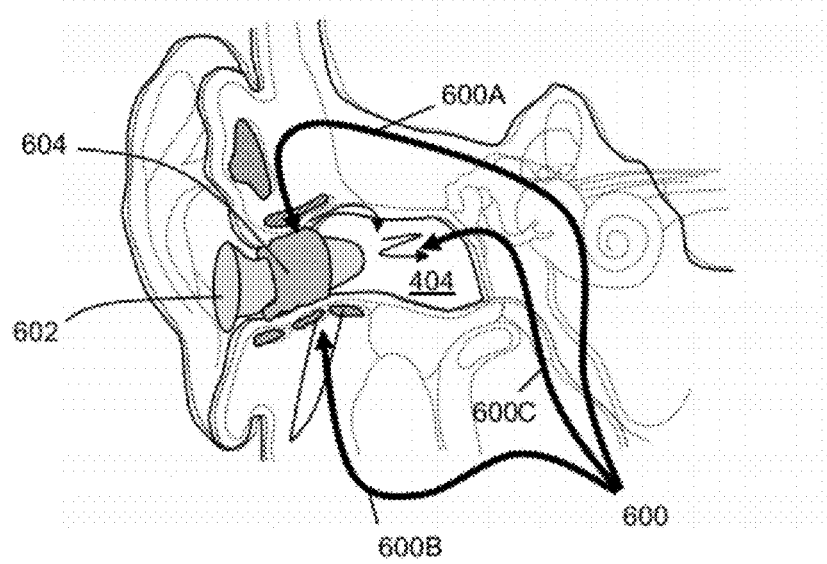
FIG. 6 illustrates a sealed or occluded ear canal in accordance with at least one exemplary embodiment.

FIG. 6 illustrates a sealed or occluded ear canal in accordance with at least one exemplary embodiment. A sealing section comprises an insertion element 602 and an expandable element 604. In a non-limiting example, insertion element 602 is a flexible element that aids in the insertion process to place expandable element 604 in an appropriate location in the ear canal. Typically, insertion element 602 is inserted centrally into the ear canal such that it does not come into contact with the ear canal wall. Insertion element 602 comprises a soft and flexible material that readily bends when contacting the ear canal wall to prevent pain or discomfort. In at least one exemplary embodiment, the length of insertion element 604 is designed so it cannot come in contact with the tympanic membrane when placed in the ear canal.

Expandable element 604 is attached to insertion element 602. Expandable element 604 is typically in a non-expanded state during insertion. In a non-limiting example, expandable element 604 is positioned on insertion element 602 such that it is positioned with its leading edge approximately half way into an average ear canal when insertion element 602 is fully inserted wherein ear canal volume 404 remains. After insertion, expandable element 602 is expanded in the ear canal and touches and forms an acoustic seal with the ear canal wall. Insertion element 602 and expandable element 604 seal an ear canal opening.

Typically, expandable element 604 contacts both the cartilaginous region and the bony region of the ear canal wall for an average user. A person with a short ear canal can have a majority or all of expandable element 604 contacting the bony region of the ear canal. Conversely, a person with a long ear canal can have a majority or all of expandable element 604 contacting the cartilaginous region of the ear canal. Ear canal volume 404 will vary from person to person. In all cases, expandable element 604 seals the ear canal and is comfortable for extended use over long periods of time. In at least one exemplary embodiment, insertion element 602 and expandable element 604 can be designed to be deeply inserted into the ear canal by increasing the length of insertion element 602. It should be also noted that insertion element 602 can include an instrument package for holding components such as transducers or electronic components.

As mentioned previously, ear canal shape and sizes can vary substantially over a large population. Insertion element 602 and expandable element 604 are designed to fit in a small ear canal opening. Expandable element 604 can then be expanded in size to seal a large or small ear canal size. Thus, insertion element 602 and expandable element 604 combine to form a component that can comfortably seal and fit a large percentage of the population. In at least one exemplary embodiment, expandable element 604 is conformal to an ear canal surface allowing a seal to be formed even if the surface is irregular in shape. A force is applied to a surface of expandable element 604 conforming and holding the surface against the ear canal wall while in use. The force is removed when the expandable element 604 is removed from the ear canal to promote easy removal.

Insertion element 602 and expandable element 604 seal an opening to the ear canal forming the ear canal volume 404 that is isolated from the ambient environment. In general, acoustic information from the ambient environment is attenuated by the sealing section. Sound can also couple to ear canal volume 404 through the body. Paths 600 illustrate areas where sound can enter. Paths 600A and 600B are bone conduction paths into ear canal volume 404. Path 600C is another path through non-bony structures such as the tympanic membrane. In at least one exemplary embodiment, the surface of expandable element 604 in contact with the ear canal wall reflects sound away from ear canal volume 404 thereby reducing the amount of sound coupled through path 600 into the ear canal.

Figure 7:
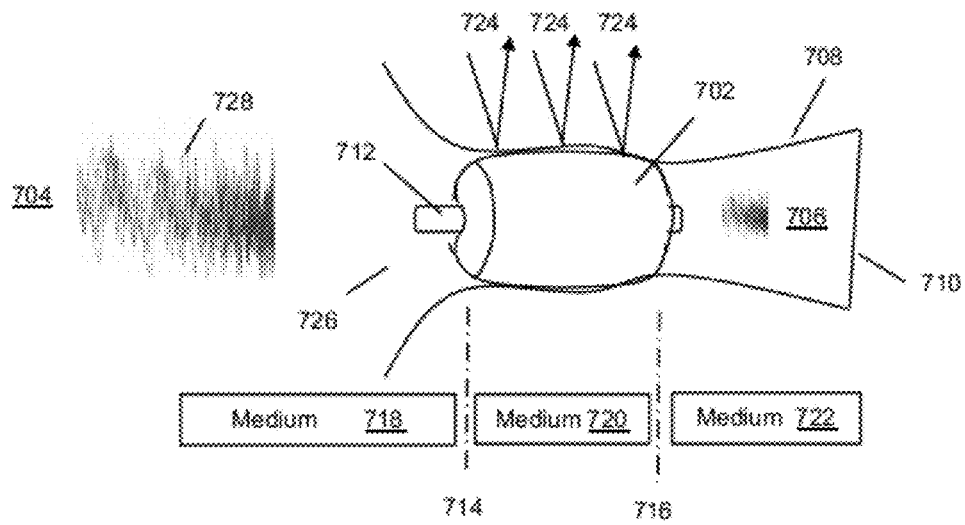
FIG. 7 is an illustration of an expandable device in an ear canal in accordance with at least one exemplary embodiment.

FIG. 7 is an illustration of an expandable device 702 in an ear canal in accordance with at least one exemplary embodiment. Expandable device 702 is inserted in an opening 726 of the ear canal and expanded to seal the ear canal from an ambient environment 704. An ear canal volume 706 is a remaining portion of the ear canal between a distal end of expandable device 702 and a tympanic membrane 710. Expandable device 702 can be designed to take up a predetermined percentage of the total ear canal volume (from a minority to majority portion). As shown, expandable device 702 takes up approximately half of the total ear canal volume.

Painful pressure (unless released) can build up in ear canal volume 706 if expandable device 702 was inserted in an expanded state. Inserting without sealing and then expanding expandable device 702 to seal the ear canal reduces pressure from building up in ear canal volume 706. A valve (not shown) can also be provided that equalizes pressure in ear canal volume 706 and ambient environment 704 when a pressure difference occurs.

In at least one exemplary embodiment, expandable device 702 is a sealed structure that can be filled with a fluid (e.g., gas, liquid, or gel) to increase volume such that the ear canal is sealed. The sealed structure can be a fixed volume or variable volume. In either a fixed volume or variable volume scenario, expandable device 702 is designed to be insertable in a small ear canal and can be expanded to fit a large ear canal thereby providing an ear canal sealing solution that covers a majority of the population. For example, a fixed volume balloon has a maximum volume designed to seal a large ear canal. The fixed volume balloon would then seal smaller ear canals requiring much less volume than the maximum volume available. Conversely, a variable volume balloon can expand or contract to the size of the ear canal from small to large. Thus, the volume of the balloon is variable. In either case, a surface of expandable device 702 is expanded to come into contact with an ear canal wall 708 of the ear canal.

There are several subjective parameters that must be met if expandable device 702 is going to achieve mainstream adoption. In general, expandable device 702 is a sealing section of an earpiece that can comprise other components (e.g. electronics, pumps, transducers, etc.) depending on the application. An earpiece is typically worn over extended periods of time. For example, eight or more hours per day. The sealing section has to be comfortable to a user. Another factor is that expandable device 702 cannot look imposing to someone placing it in their ear. In-ear devices are currently not prevalent in the market place. People may have a concern about using an in-ear device since it is unfamiliar. Thus, this negative bias can be minimized if expandable device 702 looks innocuous.

Expandable device 702 comprises a proximal surface that is directed towards ambient environment 704, a distal surface that is directed towards tympanic membrane 710, and a sidewall surface. Expandable device 702 is expanded radially until the sidewall surface contacts ear canal wall 708 and seals the ear canal. The sidewall surface of expandable device 702 is flexible and will conform to an irregular surface of ear canal wall 708 to form an acoustic seal. In at least one exemplary embodiment, the force at which the surface of expandable device 702 contacts ear canal wall 708 can be adjusted. A maximum force applied by expandable device 702 is limited to a force that will not be painful or uncomfortable to a user that has been generated by subjective measurements among a large population pool. A regulation device such as a pressure valve limits the force that can be applied. For example a gauge pressure value between about 0.0250 bar and 0.5 bar can be applied to the expandable device 702.

In a non-limiting example, expandable device 702 is a balloon structure. A stent 712 includes one or more channels for providing or removing a gas, liquid, or gel to expand or contract expandable device 702. In at least one exemplary embodiment, a pump (not shown) can be used to provide or remove the medium, which fills expandable device 702. As shown, the proximal and distal surfaces are attached to stent 712 to form a sealed structure. Stent 712 can also have acoustic channels with ports at either end. The ports on the distal end of stent 712 couple to ear canal volume 706. The ports on the proximal end can couple to devices such as transducers (for providing or receiving sound) or passively couple to ambient environment 704. Alternatively, an instrument package can also be formed in stent 712. The instrument package can include electronics, transducers, or other devices that would benefit from being in close proximity to ear canal volume 706. Wires or other interconnects would extend from a port on the proximal end of stent 712 to be coupled to other devices. The balloon surrounding the instrument package and portions of stent 712 would provide further protection from an external environment.

Modeling expandable device 702 yields a common textbook problem presented to graduate level acoustic students known as a three medium problem. Three separate volumes are identified having a boundary 714 and a boundary 716. The ambient environment 704 is a gaseous medium 718 (e.g. air). The ambient environment 704 is bounded by the proximal surface of expandable device 702. The medium (e.g. gas, liquid, gel) used to expand expandable device 702 is a medium 720. The ear canal volume 706 is bounded from medium 720 by the distal surface of expandable device 702. The medium 722 in ear canal volume 706 is a gaseous medium (e.g. air).

The problem addresses how much of the sound 728 in ambient environment 704 passes through expandable device 702 and into ear canal volume 706. In other words, the sound isolation properties of expandable device 702. An additional factor is that the proximal and distal surfaces of expandable device 702 as a balloon comprise a thin membrane or material. For example, in our test studies the balloon comprised a thin layer (less than 0.01 inches) of silicone or urethane material. Furthermore, the proximal and distal surfaces of the balloon would be thinner when expanded. In a non-limiting example of a gas filled variable volume balloon the material thickness of the balloon membrane can change from a thickness of 0.01 inches (uninflated) to 0.002 inches inflated when inflated to contact ear canal wall 708. In this example, the balloon pressure is greater than atmospheric and the balloon surfaces are under tensile stress. As commonly taught, the thin membrane would act as a low pass filter that would permit sound to pass from medium 718 to medium 720 and from medium 720 to medium 722. Thus, the prevailing theory would indicate that transmission loss from ambient environment 704 to ear canal volume 706 would be poor using expandable device 702.

A device as disclosed hereinabove was built and tested. Several unexpected results were measured and will be discussed in more detail hereinbelow. Tube measurements corresponding to the three medium problem using a pink noise source measured up to 40 dB attenuation in the frequency band for human hearing. Measurements were taken with expandable device 702 filled with a fluid and a gas. Attenuation differences were measurable depending on the medium (e.g. gas or liquid) placed in expandable device 702 but the difference was small in relation to the overall attenuation achieved by the device. Another unexpected result was that the attenuation was a function of the force applied to the surface of expandable element 702 on ear canal wall 708. The attenuation increased with rising force applied to the surface. For example, using a gas (air) to expand expandable device 702 saw a relationship between increasing attenuation with increasing pressure in expandable device 702.

Another unexpected result was the reduction in occlusion effect using expandable device 702. As mentioned above, the occlusion effect is noticeable when the ear is sealed and the person speaks. The sound in the ear canal is often unintelligible due to resonances in ear canal volume 706 and the predominance of low frequency sound. The low frequency sound from the voice is coupled to ear canal volume 706 through bone conduction and through other body paths. It should be noted that the normal path for hearing the human voice is blocked/attenuated by expandable device 702.

The sidewall surface of expandable device 702 is under tensile stress. For example, when expanding expandable device 702 with a gas the interior volume was pressurized to 1.2 atmospheres. The internal pressure not only applies a force pressing the sidewall surface to ear canal wall 708 but also puts the surface under tension. The sidewall surface of expandable device 702 acts as a reflective surface to reflect bone or body conducted sound away from ear canal volume 706 (indicated by arrows 724) thereby reducing the occlusion effect. This has enormous consequences in being able to provide a legible voice signal from within a sealed ear canal. Similarly, the proximal surface of expandable device 702 is also under tensile stress. Ambient sound 728 entering the ear canal is reflected by the proximal surface. Measurements indicate that acoustic reflectivity greater than 90% can be achieved by using a thin walled membrane under tension for frequencies in the human hearing range.

Figure 8:
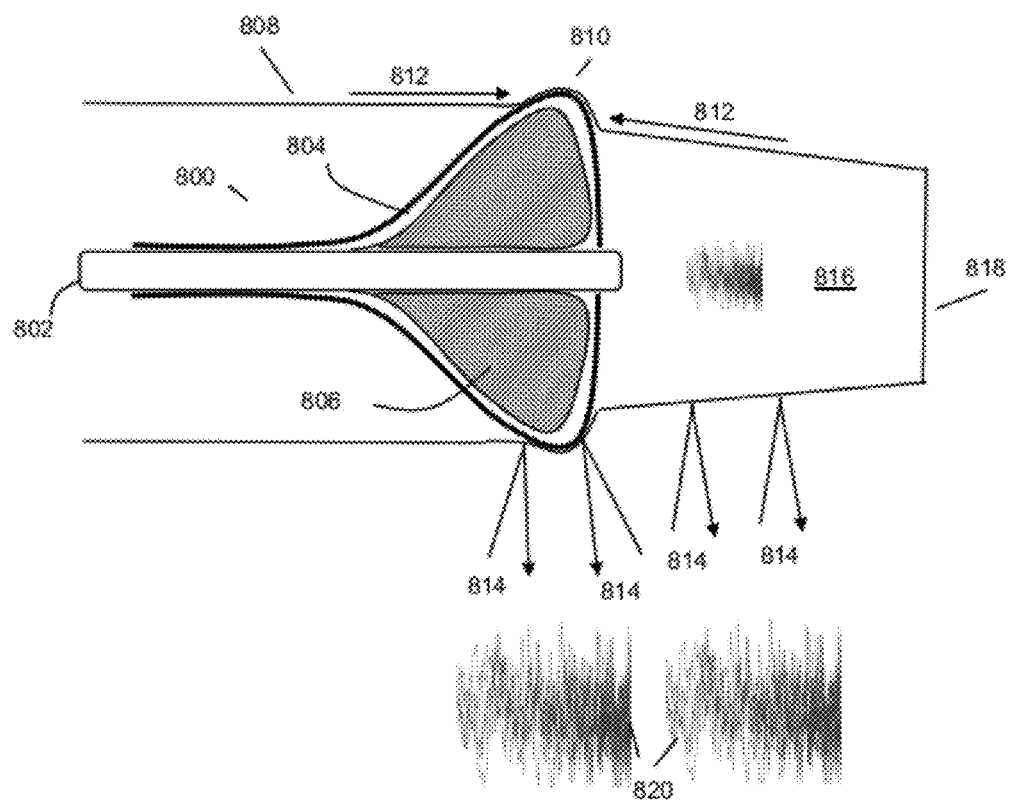
FIG. 8 is an illustration of an expanded conical shaped balloon in contact with an ear canal wall in accordance with at least one exemplary embodiment.

FIG. 8 is an illustration of an expanded conical shaped balloon 800 in contact with an ear canal wall 808 in accordance with at least one exemplary embodiment. Conical shaped balloon 800 is attached to stent 802. Stent 802 can have one or more channels for providing a path for providing and removing a gas, liquid, or gel (designated generally as 806) for expanding and contracting the device. Stent 802 can also have one or more acoustic channels coupled to ear canal volume 816. Conical shaped balloon 800 seals the ear canal forming an ear canal volume 816. Ear canal volume 816 is bounded by a distal surface of balloon 800, tympanic membrane 818, and ear canal wall 808.

The conical shaped balloon 800 differs from the oval shaped balloon of FIG. 7 having a reduced contact area for sealing the ear canal and forming an ear canal volume 816. It should be noted that the amount of contact area can be varied by molding the conical balloon shape to have an elongated contact area. The conical balloon shape has the contact area towards the distal end of the balloon. In a non-limiting example, conical shaped balloon 800 illustrates a tensioning effect on the skin of the ear canal when a force is applied by a balloon surface 804. The outward force applied by the balloon surface 804 in an area 810 of ear canal wall 808 deforms the skin layer. The ear canal wall skin layer is elastic and stretches since the surface area of the ear canal wall 808 has been increased by the deformation. The stretching of the ear canal wall skin layer due to deformation is indicated by arrows 812 and would occur circumferentially around ear canal wall 808. In general, the thick skin layer in the cartilaginous region would deform more than the thin skin layer in the bony region of the ear canal.

As mentioned previously, balloon 800 has a thin membrane that is under tensile stress pressed against ear canal wall 808 that seals ear canal volume 816 from the ambient environment. A portion of the sound normally conducted through bone and other internal paths (e.g. speech, chewing, etc.) into ear canal volume 816 is reflected away from the ear canal thereby reducing the occlusion effect. The amount of occlusion effect mitigation could not be entirely attributed to reflection by balloon 800. The occlusion effect is further mitigated by the process of stretching ear canal wall 808 using balloon 800. Deformation of ear canal wall places the skin layer and underlying tissues under tensile stress much like the head of a drum. Similar to balloon surface 804, the stretched skin layer of ear canal wall 808 is a sound reflective surface. The occlusion effect mitigation from ear canal wall 808 is illustrated by sound 820 coming from the body and being reflected away from ear canal volume 816 as shown by arrows 814. Ear canal volume 816 is a sealed volume that has resonances that can increase the amplitude of certain frequencies while reducing others. As described above, this is most noticeable with a sealed ear canal and user speech. Measurements and subjected testing have conclusively shown that the occlusion effect is substantially decreased by reducing the amount of body-conducted sound to ear canal volume 816.

Another aspect of creating an acoustic seal in the ear canal is that it is also a watertight seal. People who are prone to ear infections or spend a lot of time in water such as a swimmer wear ear plugs. In a non-limiting example, balloon 800 can be used as an ear plug for preventing a liquid from entering the ear canal. For example, prior to an event where a liquid can enter the ear, a user places a balloon 800 in each ear, inflates balloon 800 to seal the ear canal, and then engages in the event. After finishing the event the user deflates balloon 800 and removes balloon 800. Balloon 800 will have prevented the ear canal from getting wet. In at least one exemplary embodiment, balloon 800, balloon valving, and balloon pump are housed together in a single unit for ease of use.

A problem with many earpieces having an in-ear device is maintaining the seal over an extended period of time under a wide variety of conditions. In particular, stability of the earpiece when a person is moving such as running or exercising is difficult to achieve. As disclosed above, ear canal wall 808 is slightly deformed by the internal pressure that provides a radial force that pushes surface 804 against ear canal wall 808. The deformation makes it difficult to dislodge balloon 800 even under vigorous movement. Moreover, in testing, balloon 800 is able to support a typical housing having electronics, transducers, battery, and other components for an earpiece without breaking the seal and maintaining a high level of comfort. Thus, deforming ear canal wall 808 circumferentially in the ear canal is a very stable method for holding an earpiece in place.

FIG. 9 is a graph 900 illustrating sound isolation as a function of inflation of an inflatable system in accordance with at least one exemplary embodiment. The inflatable system as disclosed hereinabove, seals an opening of an ear canal isolating the remaining ear canal volume from the ambient environment. Them measurement is made in a tube. An inflatable system is inserted in the tube forming a first region, the balloon, and a second region. In the first region of the tube, pink noise 902 is provided to a first side of the inflatable system that is measured by a microphone. In the second region (isolated by the inflatable system) measurements are taken by a second microphone. The amount of sound isolation provided by the inflatable system is the difference in the measured sound levels in the first and second regions. The tube in the second region is extended to a length where signal reflection is not a measurement issue (e.g. there is no reflected signal received by the second microphone). Additionally, the inflation medium can be either a liquid, gas, gel, or other medium to increase/decrease the pressure within the inflatable system to form a seal that isolates the second region from the first region.

In at least one exemplary embodiment, the inflatable system is a gas filled balloon. The diameter of the balloon increases as it is inflated. The balloon creates an acoustic seal when the balloon surface contacts the tube wall. Raising the pressure within the balloon increases the radial force pressing the balloon surface against the tube wall.

The curve 904 represents the measurement when the inflatable system is not completely sealed. Prior to an acoustic seal being formed, a portion of pink noise 902 passes through openings coupling the first region to the second region. The measured signal in the second region will vary in intensity across the frequency band. The portion of curve 904 that is above the pink noise signal is due to resonance 906 in the second region. As shown, both the low frequency and high frequencies are attenuated in the second region.

A curve 908 represents the inflatable system at a first pressure P1 greater than or equal to a seal pressure where the inflatable system has conformed to the inside of the tube. There is a distinct drop between the sound pressure level from the first region to the second region when the inflatable system forms an acoustic seal with the tube. This is indicated by curve 908 being less than curve 902 at all frequencies. Typically, the amount of isolation is not constant but varies over frequency. A curve 910 represents the inflatable system inflated to a second pressure P2 greater than pressure P1. Increasing the pressure in the inflatable system provides improvement of the attenuation properties of the system.

The principal of increasing and decreasing pressure can be used to enhance protection of an earpiece user. The inflatable system can be kept at the sealing value pressure (or slightly greater) under normal operating conditions to maximize comfort to the user. For example, minimum pressures can be used under moderate noise levels where the measured sound pressure levels and SPL_Dose does not indicate a potential harmful situation to the user. Furthermore, an earpiece can have circuitry for measuring sound pressure level. Upon detecting a rise in sound pressure level (e.g. greater than 1 dB) or to mitigate potential hearing damage to the user the inflatable system pressure can be increased to raise the attenuation of ambient noise thereby providing further protection. Conversely, detecting benign conditions in the ambient environment, the earpiece could lower the pressure in the inflatable system. Thus, the level of attenuation can be varied corresponding to pressure within a range that is comfortable to the user.

FIG. 10 is a graph 1000 of sound isolation versus occlusion effect in accordance with at least one exemplary embodiment. The occlusion effect was measured for a sealed ear canal. In general, a sealing section having a surface comprising sound reflective material was held against an ear canal wall. In at least one exemplary embodiment, the sound reflective material was under tensile stress to increase the material reflectivity. The force holding the sound reflective material against the ear canal wall also deforms and stretches the elastic skin layer. The sealing section and the stretched ear canal skin layer reflects sound propagating through the body away from the ear canal.

In a non-limiting example, the sealing section is an expanding device such as a balloon. Graph 1000 shows that the occlusion effect is reduced as attenuation is increased. Conversely, the occlusion effect increases as the attenuation decreases. As disclosed above, increasing pressure of the balloon increases attenuation between the ambient environment and the ear canal. Increasing pressure also increases the tensile stress on the surface material of the balloon and further deforms and stretches the ear canal skin layer. The result of which is improved reflectivity of body propagated sound away from the ear canal thereby reducing the occlusion effect.

Figure 11:
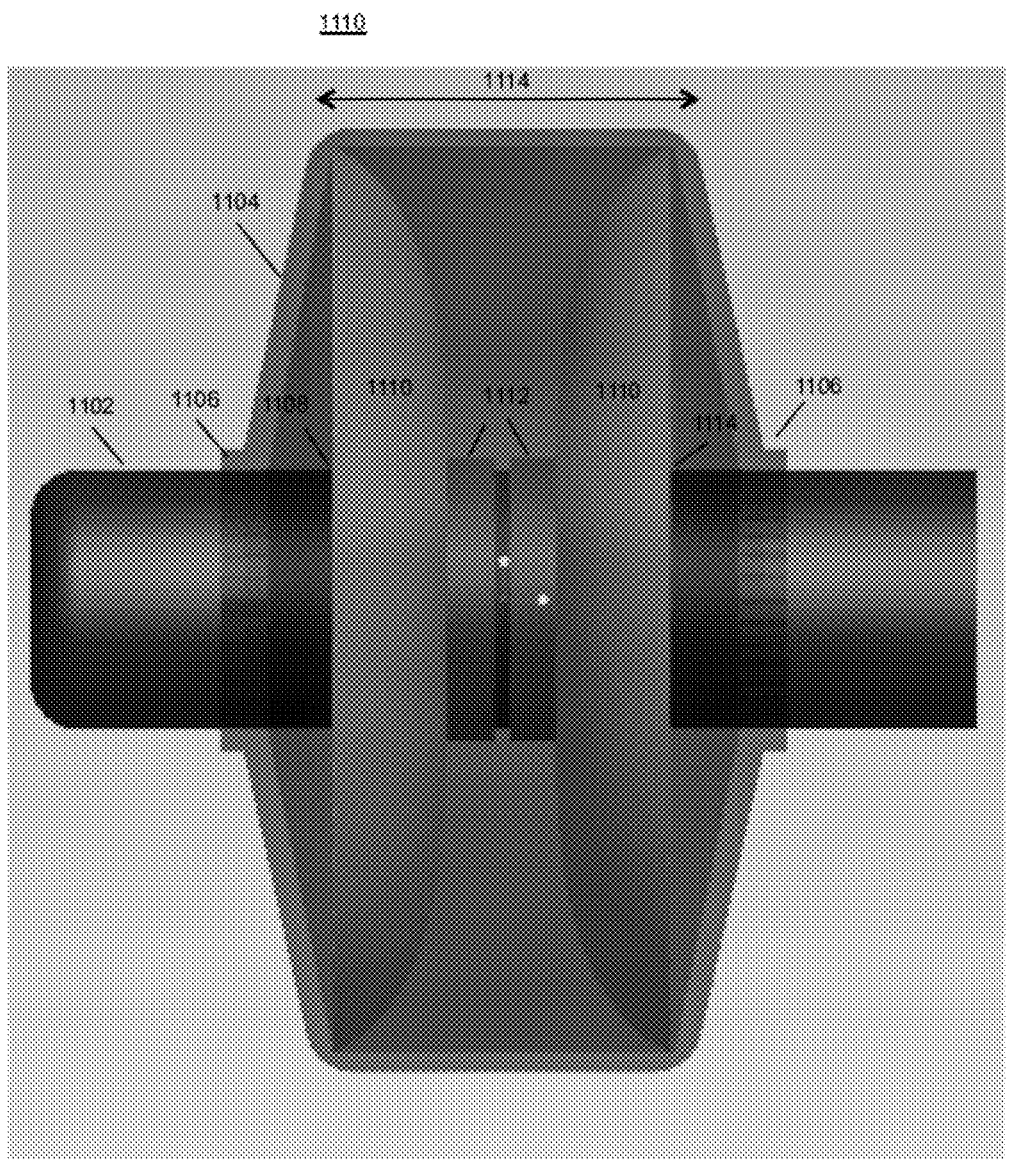
FIG. 11 is an electro-active polymer expandable device in accordance with at least one exemplary embodiment.

FIG. 11 is an electro-active polymer expandable device 1100 in accordance with at least one exemplary embodiment. Expandable device 1100 comprises a stent 1102, a membrane 1104, and electro-active polymer elements 1110. In a non-limiting example, membrane 1104 is a flexible material such as silicone, urethane, or other flexible material. Membrane 1104 can be a sealed or unsealed structure.

In at least one exemplary embodiment, membrane 1104 is a sealed balloon type structure. Membrane 1104 is attached to stent 1102 at collars 1106. For example, collars 1106 can be laser welded to stent 1102 or attached by adhesive to ensure a seal. If a membrane is used, a portion of a membrane connected to a structure (base membrane) can be made of any material, rigid or elastic, including various plastic or metal materials, or it can be made of a membrane formed of thin rubber-based material, deformable plastic or silicone-based materials or other elastomeric materials suitable for a given application. If the base is configured as a flexible membrane, the cavity can more easily conform to a product's surface, thereby increasing the ease with which the cavity can be installed, removed, and replaced. Likewise, the outer membrane also can be made of a thin rubber-based material, deformable plastic or silicone polymer materials, or other elastomeric materials suitable for a given application. If the base membrane and outer membrane are made of silicone material, both should be from 0.50 mm to 2.5 mm in thickness. In this regard, the base may be a membrane instead of a piece of rigid material. The edges of the outer membrane and the base membrane can be mechanically fastened or clamped forming the membrane cavity. Additionally, at least a portion of the base membrane can be adhesively attached (e.g., adhesive tape, glue) or mechanically fastened to the support structure.

Electro-active polymer elements 1110 comprise an electro-active polymer. Electro-active polymers (EAPs) are touted as the basis for future artificial muscles. EAPs can be deformed repetitively by applying external voltage across the EAP. They can quickly recover their original configuration upon reversing the polarity of the applied voltage. The electromechanical properties of the EAP under dry and moist conditions are presented along with the EAP's performance under load conditions. As is well known, the EAP has a high load bearing capacity to mass ratio, short response time, and nearly linear deformation response with respect to applied voltage.

Artificial muscle polymers can be formed from a conductive polymer doped with surfactant molecule or from an ionic polymer metal composite (IPMC). Doped electroactive polymers (EAPs) are conductive polymers (e.g., polypyrrole or polyanaline) doped with a surfactant (e.g., sodium dodecyl benzene sulfonate). IPMCs typically consist of perfluorsulfonate polymers that contain small proportions of sulfonic or carboxylc ionic functional groups. Nafion®, a polymer made by DuPont, is one example of a poly(tetrafluoroethylene) based ionomer. For its application as an artificial muscle, Nafion® can be produced in a sheet geometry with positive counter ion (e.g., Na+ or Li+) contained in the matrix. The outer surface region (less than a micrometer) of the polymer sheet is then impregnated with a conductive metal such as platinum or gold. The resulting EAP polymer can absorb water until its physical ability to expand is balanced by the affinity of water for the polymer-fixed ions and free counter ions. When an electrical field is applied across the EAP, the EAP deforms as a result of stresses generated by the movement of water and mobile positive ions in the polymer composite.

The general structure of Nafion® can be used for example (a) where x=6-10 and y=z=1. The properties of the polymer of the type shown in (a) can be changed by varying the values of x, y and z. A similar perfluorsulfonate polymer with shorter side chains is produced by Dow (b) where x=3-10, y=1 and z=0. The EAP can be easily deformed upon the application of low voltage (approximately 1-3.5 V). Deflection varies linearly at low applied voltages (<1 V) with nonlinear behavior observed at higher voltages. At the linear range the EAP deforms at a rate of about 20-35 degrees/volt. The magnitude of deflection of the EAP strip (measured in degrees of deflection) is similar in both directions (upon reversing the polarity of the electrical field). This suggests that the EAP surfaces have similar conductivity and that the EAP composition is reasonably uniform. However, the EAP strip can at times deflect significantly more in one direction and the change in deflection variation with voltage is non-linear. In the above cases resistance measurements can be used to verify if the less conductive side of the EAP is contact with the negative electrode which would result in the observed reduction in bending. Such a behavior is believed to be due to either loss of positive counter ions in the matrix (due to repeated soaking of the EAP in water) or imperfections in the EAP conductive surface. For the specific EAP tested in this illustration the change in deflection with applied voltage was greater above about 2.5 V. In other words, at higher voltages to the EAP the applied voltage causes a greater deflection per volt than at low voltages.

In at least one exemplary embodiment, an EAP performs well when immersed in water. The deflection is somewhat less than in air given the additional work that the EAP strip has to perform in order to displace water as it deforms. The deflection of the EAP in water is more consistent and the electromechanical response does not change significantly over 20-30 minutes. Thus, in a non-limiting example membrane 1104 is filled with a fluid such as water.

EAP response time can be measured as the time it takes an EAP strip to deform to its final equilibrium position under different applied voltages. For example, the response time (for a 5"×0.6" EAP strip) was determined to increase with increasing voltage at a rate of about 5.2 seconds/volt. However, the rate at which the response time increases decreases as the voltage increases. The speed (or rate) of deformation can also be evaluated in terms of degrees of deflection/second. For the above EPA strip the deformation speed increased with the applied voltage up to about 7 degrees of deflection/sec; however, the increase in deflection speed was progressively less as the applied voltage increased above about 1.5 V. The EAP deformation is governed by attraction of the positive counter ions to the negative electrode (Cathode). This attractive force increases with increasing applied voltage. As a result, the EAP strip bends at a faster rate as the applied voltage is increased. The decrease in electromechanical response of the EAP, when operating in air, is attributed to evaporation of water from the EAP strip. Therefore, it is expected that the resistance of the electrical resistance of the EAP would increase with time (after re-wetting and then exposure to air). This can be confirmed by measuring the electrical resistance of the EAP strip in the middle and near the edges of the EPA strip. The resistance of the EAP will increases with time as the water in the strip is squeezed away from the region held by the electrodes. Subsequent water evaporation from the electrode area, already depleted of water, eventually results in a "jump" in the resistance likely due to loss of mobile water. As a result the mobility of counter ions inside the strip, near the electrodes, is virtually eliminated. As time progresses, water which was squeezed away from the compressed electrode region diffuses back to that region thereby allowing for some restoration of counter ion mobility as suggested by the slight decline of the resistance after the "jump".

The maximum lifting ability of the EAP strip typically shows a linear increase of the maximum weight lifted with the applied voltage, at a rate of about 1.2 g/V for the strip tested in the present study. The force output of the EAP, defined here as the ratio of the maximum weight lifted by the EAP relative to its own weight, also increases linearly with the applied voltage. The rate at which the force output increases is nearly constant at 20 (g lifted/g EAP)/V. When the EAP strip length is halved (wing configuration), the maximum weight lifted, at a given voltage, should be similar to that obtained by the longer strip; however, the force output to voltage ratio would be doubled. The above behavior indicates that the flexural strength of a shorter strip is greater, although the extent of deflection is smaller. A definitive theory to explain the mechanism of EAP deformation is yet to emerge. However, based on the composition of the EAP, its performance when subjected to an electrical field, and the requirement for the presence of positive counter ions and water for its operation suggest a possible operational mechanism.

Upon the application of an electrical field across a moist EAP, which is held between metal electrodes attached across a partial section of an EAP strip, bending of the EAP is induced. Positive counter ions move towards the negative electrode (cathode), while negative ions that are fixed (or immobile) to the polymer (e.g. $SO_3$) experience an attractive force from the positive electrode (anode). At the same time, water molecules in the EAP matrix diffuse towards the region of high positive ion concentration (near the negative electrode) to equalize the charge distribution. As a result, the region near the anode swells and the region near the cathode de-swells, leading to stresses which cause the EAP strip to bend towards the positive anode.

In a non-limiting example, electro-active polymer elements 1110 are formed as a concave structure. Electro-active polymer elements 1110 includes collars 1112. Collars 1112 are attached to stent 1102. For example, an adhesive can be used to attach collars 1112 to stent 1102. The outer lip 1108 of elements 1110 are in contact with membrane 1104. Elements 1110 support membrane 1104 as shown in the diagram.

Elements 1110 have a first electrode on the concave surface and a second electrode on a convex surface. The first and second electrodes are coupled to conductors (not shown) housed in stent 1102. The conductors are coupled to circuitry (not shown) for providing a variable voltage to elements 1110. In at least one exemplary embodiment, elements 1110 are unbiased (zero volts) as shown in FIG. 11. Elements 1110 in the unbiased condition hold membrane 1104 under tensile stress to a width indicated by double-sided arrow 1114. Membrane 1104 can be compressed and fitted into an ear canal. Elements 1110 contribute a radial force that holds membrane 1104 against the ear canal wall.

Figure 12:
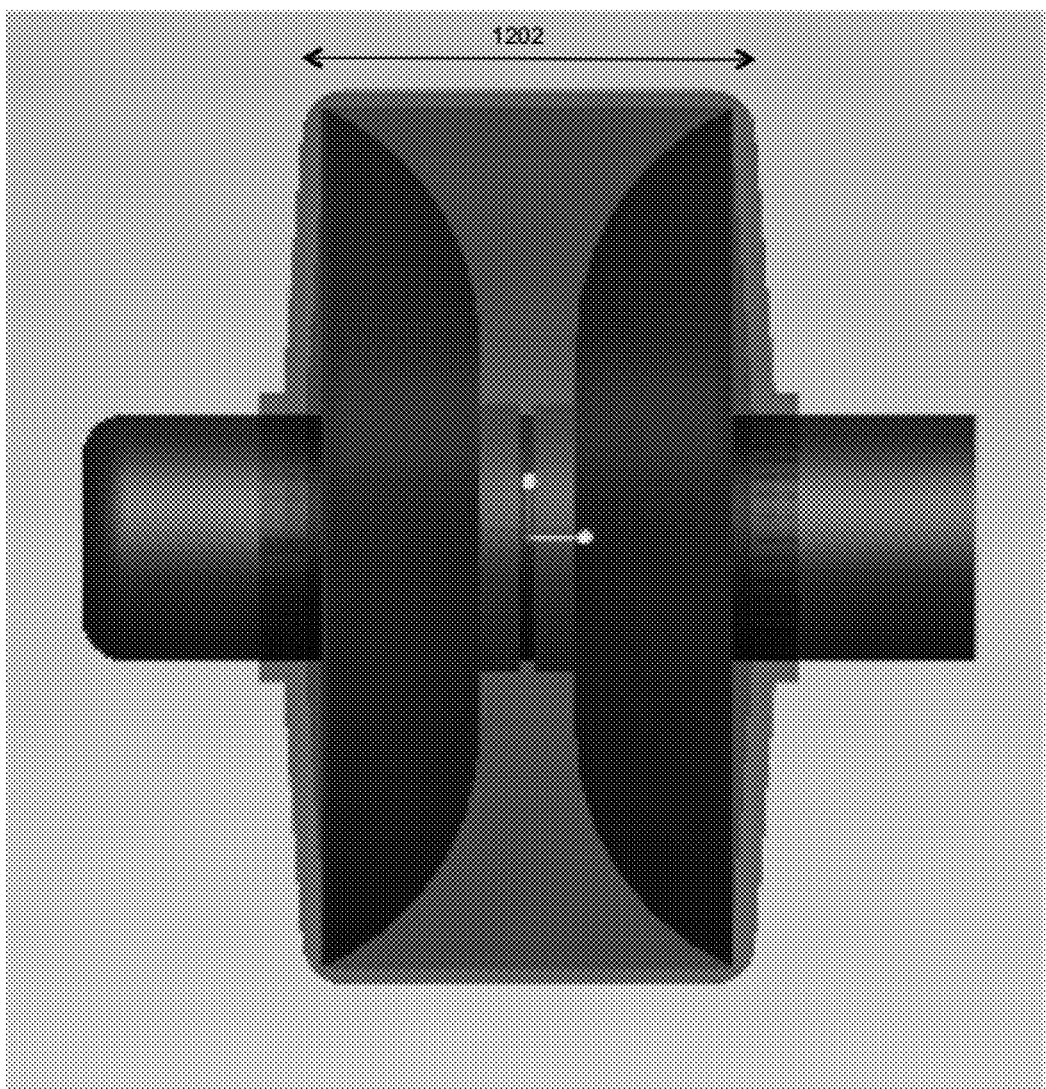
FIG. 12 is an electro-active polymer expandable device in accordance with at least one exemplary embodiment.

FIG. 12 is an electro-active polymer expandable device 1200 in accordance with at least one exemplary embodiment. A voltage is applied across the first and second electrodes of elements 1110. The applied voltage on the electro-active polymer causes the elements 1110 to deflect in a manner that increases the tensile stress on membrane 1104. As shown, the deflection increases a distance 1202 on membrane 1104 such that distance 1202 is greater than distance 1114 of FIG. 11. Thus, a mechanical means has been provided for increasing tensile stress on a membrane and seal an ear canal opening. By increasing the voltage across the electro-active polymer material of elements 1110 the tensile stress on membrane 1104 is raised to increase reflection of sound propagated through the body away from the ear canal thereby reducing the occlusion effect.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. An acoustic reflective device comprising:
   a membrane; and
   a stressing device, where the stressing device is operatively attached to the membrane, where the stressing device increases a stress in the membrane in response to an input, and where the increase in the stress changes an acoustic reflectivity of the membrane,
   where the stressing device includes:
   an electroactive polymer element;
   a first electrode; and
   a second electrode, where the first electrode contacts a first side of the electroactive polymer element, and the second electrode contacts a second side of the electroactive polymer element, where the input is an electric potential difference applied between the first and second electrodes, where when the electric potential difference is applied between the first and second electrodes a strain of the electroactive polymer element increases on the first side, where the first side is operatively attached to the membrane and as the strain increases on the first side the membrane is stressed.

2. The acoustic reflective device according to claim 1 where the stressing device includes:
an inflatable membrane, where the inflatable membrane is operatively attached to the membrane or the membrane is at least a portion of the inflatable membrane, and
a fluid in the inflatable membrane, where when the electric potential difference is input into the inflatable membrane the inflatable membrane undergoes a strain increase, and where as the strain increases the membrane is stressed.

3. An acoustic reflective device comprising:
a membrane; and
a stressing device, where the stressing device is operatively attached to the membrane, where the stressing device increases a stress in the membrane in response to an input, and where the increase in the stress changes an acoustic reflectivity of the membrane,
where the input includes first and second inputs, where the stressing device includes:
a first electroactive polymer element;
a second electroactive polymer element;
a first electrode;
a second electrode, where the first electrode contacts a first side of the first electroactive polymer element, and the second electrode contacts a second side of the first electroactive polymer element, where the first input is a first electric potential difference applied between the first and second electrodes, where when the first electric potential difference is applied between the first and second electrodes a strain of the first electroactive polymer element increases on the first side of the first electroactive polymer element, where the first side of the first electroactive polymer element is operatively attached to the membrane;
a third electrode; and
a fourth electrode, where the third electrode contacts a first side of the second electroactive polymer element, and the fourth electrode contacts a second side of the second electroactive polymer element, where the second input is a second electric potential difference applied between the third and fourth electrodes, where when the second electric potential difference is applied between the third and fourth electrodes a strain of the second electroactive polymer element increases on the first side of the second electroactive polymer element, where the first side of the second electroactive polymer element is operatively attached to the membrane, where and as the strain increases on at least one of the first side of the first electroactive polymer element and the second electroactive polymer element the membrane is stressed.

4. The acoustic reflective device according to claim 1, where the electric potential difference is between about 0.5 and 15 volts.

5. The acoustic reflective device according to claim 3, where the first electric potential difference and the second electric potential difference are between about 0.5 and 15 volts.

6. The acoustic reflective device according to claim 2, where the fluid is at least one of a liquid and a gas.

7. The acoustic reflective device according to claim 2, where the fluid in the inflatable membrane results in an internal gauge pressure between about 0.5 bar and 1.5 bar.

8. The acoustic reflective device according to claim 1 where the membrane is at least one of oval-shaped or conical shaped.

9. The acoustic reflective device according to claim 1 where the acoustic reflective device is configured to stretch a wall of an ear canal via the membrane.

10. The acoustic reflective device according to claim 1 where the acoustic reflective device is configured to reflect transmitted sound at an interface between a wall of an ear canal and the membrane via the acoustic reflectivity of the membrane.

* * * * *